(12) United States Patent
Djupesland et al.

(10) Patent No.: US 7,377,901 B2
(45) Date of Patent: May 27, 2008

(54) APPARATUS FOR COLLECTION OF AIRWAY GASES

(75) Inventors: Per Djupesland, Osto (NO); Wei Qian, Ontario (CA)

(73) Assignee: Optinose AS, Oslo (NO)

( * ) Notice: Subject to any disclaimer, the term of this patent is extended or adjusted under 35 U.S.C. 154(b) by 98 days.

(21) Appl. No.: 10/312,242

(22) PCT Filed: Jun. 19, 2001

(86) PCT No.: PCT/IB01/01300

§ 371 (c)(1),
(2), (4) Date: May 29, 2003

(87) PCT Pub. No.: WO01/97689

PCT Pub. Date: Dec. 27, 2001

(65) Prior Publication Data

US 2004/0024330 A1 Feb. 5, 2004

(30) Foreign Application Priority Data

Jun. 21, 2000 (GB) ................................. 0015309.8

(51) Int. Cl.
| | |
|---|---|
| *A61B 5/02* | (2006.01) |
| *G01N 1/22* | (2006.01) |
| *G01N 31/00* | (2006.01) |
| *G01N 33/497* | (2006.01) |
| *B32B 5/02* | (2006.01) |
| *B32B 27/04* | (2006.01) |
| *B32B 27/12* | (2006.01) |

(52) U.S. Cl. ............... 600/529; 600/532; 600/543; 73/23.3; 422/84

(58) Field of Classification Search .............. 600/532; 73/23.3; 42/84
See application file for complete search history.

(56) References Cited

U.S. PATENT DOCUMENTS

| | | | |
|---|---|---|---|
| 5,335,656 A | | 8/1994 | Bowe et al. |
| 6,010,459 A | | 1/2000 | Silkoff et al. |
| 6,033,368 A | * | 3/2000 | Gaston et al. ............. 600/532 |
| 6,053,874 A | * | 4/2000 | Kharitonov et al. ........ 600/543 |
| 6,067,983 A | | 5/2000 | Stenzler |
| 6,419,634 B1 | * | 7/2002 | Gaston et al. ............. 600/532 |
| 6,585,661 B1 | * | 7/2003 | Hunt et al. ................ 600/532 |
| 6,626,844 B1 | * | 9/2003 | Alving et al. ............. 600/532 |
| 6,723,056 B1 | * | 4/2004 | Alving et al. ............. 600/543 |
| 2003/0208131 A1 | * | 11/2003 | George ...................... 600/532 |

OTHER PUBLICATIONS

Djupesland, P.G.; Qian, W.; Chatkin, J.; and Haight, J.S.J. for "Improved Method for Off-line Measurements of Nitric Oxide from Pulmonary and Nasal Airways" (Abstract Jun. 21, 2000).

* cited by examiner

*Primary Examiner*—Robert L Nasser
(74) *Attorney, Agent, or Firm*—Proskauer Rose LLP; Kristin H. Neuman, Esq.

(57) ABSTRACT

The invention relates to an apparatus for collection of airway gases from a subject comprising a first means for producing closure of the velum of the subject, and a second means for collection of the airway gases, wherein the first and second means need not be integral with each other.

36 Claims, 15 Drawing Sheets

APPARATUS FOR COLLECTION OF AIRWAY GASES

Figure 1:
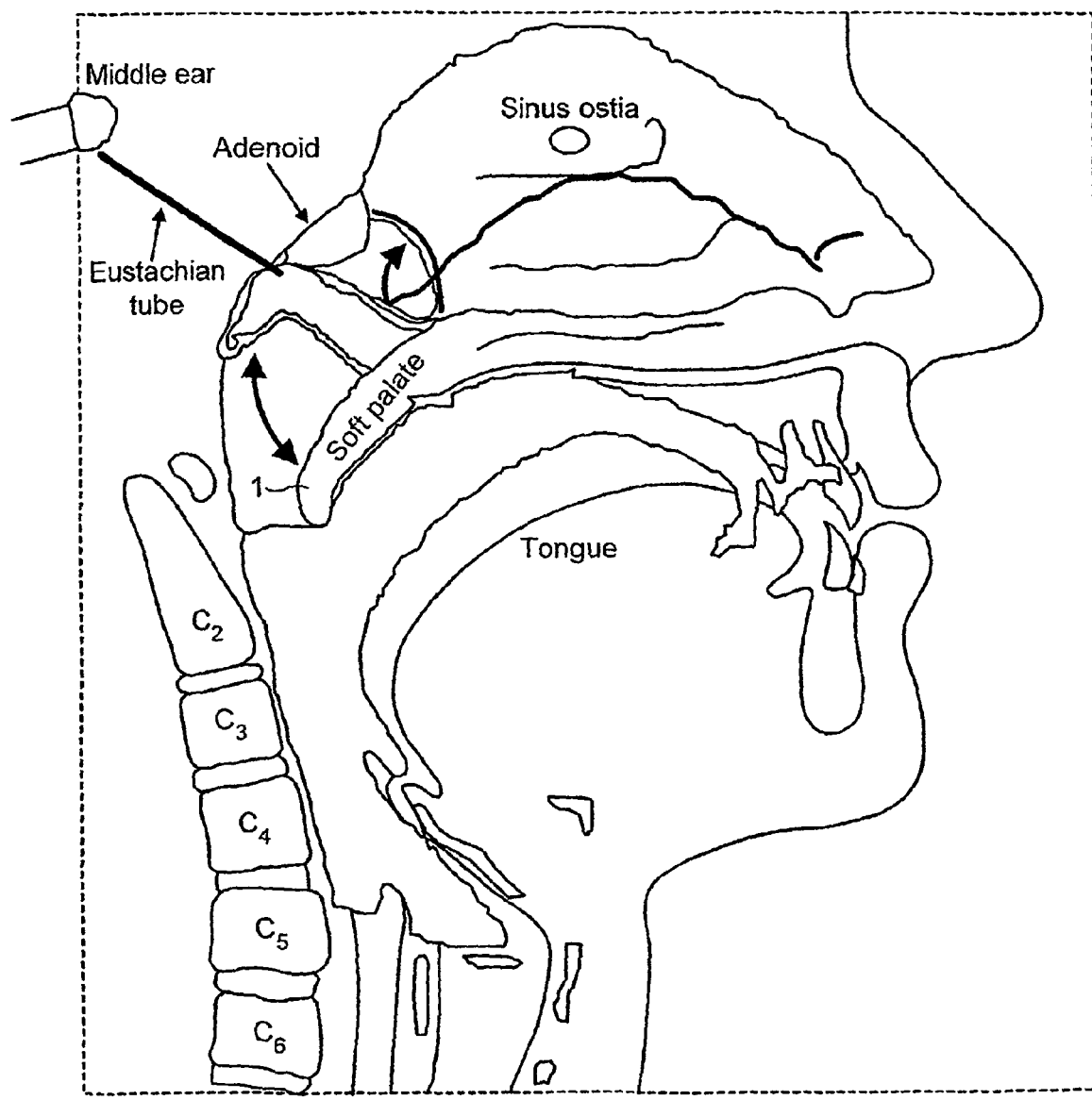

The present invention relates to an apparatus and to a method of using same.

In particular, the present invention relates to a method and an apparatus for the collection of gases originating from the airways.

More in particular, the present invention relates to a method and an apparatus for the collection of condensates from gases originating from the airways.

Analysis of gases and condensates from the airway of humans and animals can provide valuable information on biochemical and physiological processes in health and disease. Such analysis can also provide information on the effects of different types of exposures, interventions and therapies.

By way of example, the analysis of airway gases and/or condensate from airway gases can present a powerful diagnostic technique which may be used in the detection or monitoring of a variety of conditions. By way of example, the fields of diagnostic usage include: asthma, gastric ulcer (eg. *Helicobacter pylori*—currently a widely used examination), liver diseases, pancreatic diseases, kidney diseases, metabolic disorders—such as diabetes and other endocrine disorders, inborn errors of metabolism, detection of alcohol in breath, detection of drugs in breath and many others.

It is likely that the market will expand as gas and condensate collection becomes a common diagnostic procedure for clinical and home monitoring of a variety of diseases.

To date, methods for remote collection in bags for subsequent analysis of gases such as nitric oxide (NO) have been developed for air exhaled from the lower airways.

However, analysis of the contents and concentration of particles, gases and other volatile or liquid chemical substances released from the airways (or other organs), frequently requires technologically advanced and expensive non-portable equipment.

In addition, methods that rely on the remote collection in bags for subsequent analysis of gases have shortcomings as do the current methods for the storage and transportation of such gases. Typically, the shortcomings relate to the elimination of the dead-space, contamination from adjoining airways (nasal collection) as well as the properties of the storage vessel.

Thus, the prior art methods for bag collection during tidal breathing and single flow and pressure controlled exhalation impose several methodological problems when applied to the nasal airway. Firstly, the exhaled air will necessarily be contaminated from gases originating from the lower airways and oropharyngeal spaces. Secondly, despite control of the total exhalation flow, the partition of flow between the two passages remain unknown. Due to the flow dependent aerodynamics of the complex nasal airway, this may potentially induce an underestimation of actual nasal output of gases and substances in condensate. Finally, even if unilateral anterior occlusion is used, gases and condensate may escape through the posterior nasal opening and contaminate the air exhaled through the patient side.

Due to the physiological cyclic alternation pattern of reciprocal congestion and decongestion of nasal mucosa, the distribution of airflow between the parallel nasal passages remain unknown. The flow rate will influence not only the concentration, but also the output due to flow-related changes in nasal airflow characteristic in the complex nasal passage. Thus, exhalation of air through the nasal passages in parallel is not reliable. Exhalation with one nostril occluded solve the problem of uneven distribution, but the air exhaled unilaterally will be contaminated form from air escaping from the posterior opening of the contralateral nasal passage (choanal aperture).

In conclusion, the bag collection techniques of the prior art have inherent sources of error limiting reliability of collection of gases from the nasal airways.

In addition, and at present, the collection of airway gases or breath relies on expensive bags and plastic equipment for medical use.

In addition, there already exist means for the bag-collection of exhaled gas. However, these methods cannot be used for nasal gases, and cannot be used for collection of condensate.

In addition, the bags currently used for gas collection are very expensive—in addition to their other disadvatages as described herein.

Thus, the collection of airway gases using the current devices can be a serious problem, requiring expensive and advanced analysers.

The present invention seeks to overcome some or all of the problems associated with the prior art devices.

Aspects of the present invention are presented in the claims. These aspects and other aspects of the present invention are now discussed in detail below.

Thus, in one aspect, the present invention provides an apparatus for the collection of airway gases from a subject comprising a) a first means for producing closure of the velum of the subject; and b) a second means for collection of the airway gases, wherein the first and second means need not be integral with each other.

The velum is otherwise known as the soft palate—which is shown in FIG. 1 (shown by arrow 1). The direction of movement of the velum is presented by way of the double headed arrow (marked by arrow 2).

Preferably the first and second means are integral with each other. By way of example, they can be releasably fitted to each other.

In another aspect, the present invention provides a method of collecting nasal gas from a subject, said method comprising a) producing closure of the velum of the subject, and b) collecting nasal gases, said gases preferably being collected by i) aspiration of nasal gases, or ii) nasal insufflation.

In another aspect, the present invention provides a method of simultaneously collecting gases from a subject from the lower airway and the nasal airway, said method comprising a) producing closure of the velum of the subject, b) collecting exhaled gases from the airway, and at the same time, c) collecting nasal gases, said gases preferably being collected by i) aspiration of nasal gases, or ii) nasal insufflation.

In another aspect, the present invention provides an apparatus for collection of exhaled gas condensate from a subject, said apparatus comprising a) a first means for producing closure of the velum of the subject, b) a second means for collecting exhaled gases, and c) a third means for causing condensation from said exhaled gases.

Preferably the first, second and third means are integral with each other. By way of example, they can be releasably fitted to each other.

In another aspect, the present invention provides an apparatus for collection of nasal gas condensate from a subject, said apparatus comprising a) a first means for producing closure of the velum of the subject, b) a second means for aspirating nasal gases, c) a third means for causing condensation from said nasal gases.

Preferably the first, second and third means are integral with each other. By way of example, they can be releasably fitted to each other.

In another aspect, the present invention provides a method for simultaneously collecting gases from nasal cavities and lower airways of a subject in series, said method comprising a) producing closure of the velum of the subject, b) collecting exhaled gas, and at the same time c) insufflating nasal cavities with exhaled gas, and d) collecting gas from the nasal cavities.

In another aspect, the present invention provides a method or apparatus for the analysis of airway gases wherein a) gases are collected according to the present invention, b) concentration of one or more of said gases is determined.

Preferably the apparatus comprises analytical means for analysing the collected airway gases or one or more components thereof.

The apparatus and method of the present invention are advantageous for a number of reasons.

By way of example, the results obtained with the method of the current invention for collecting exhaled gas are better that the results obtained using this bag-collection method.

In addition, the apparatus of the present invention can be less expensive—and easier, cheaper and safer to transport,—than the prior art devices. Moreover, the apparatus of the present invention may be re-used.

The ease, simplicity and non-invasiveness are good advantageous features of the gas collection apparatus according to the present invention.

Also, the apparatus of the present invention provides a simple, reliable and economical means for the remote collection airway gases and condensate.

In a prefered aspect, the NO is determined.

Here, the simultaneous collection of NO gas from the lungs and from the nose using the apparatus of the present invention does not require any external pump or suction, and dramatically reduces the costs of performing such tests, as well as making the tests substantially easier to perform Analysis of NO is preferred since there have been earlier reports that NO is a gas which can be analysed in airway gases to assist in monitoring of certain conditions. However, other gases can be analysed. By way of example, recent studies have suggested carbon monoxide and penthane as other markers of airway inflammation. Urease in exhaled air can be also used to and diagnose infection with *Helicobacter pylori* causing stomach ulcer.

Preferably, the method comprises subsequently analysing the collected airway gases or one or more components thereof.

As indicated above, the disadvantages and shortcomings of current methods for remote collection of gases (bag collection) and condensate (frozen condensate during tidal breathing) can be overcome using the apparatus and method of the present invention. Moreover, the apparatus and method of the present invention improve the simplicity of collection. In addition, the apparatus and method of the present invention enable workers to extend the field of application.

The apparatus of the present invention can even used to reliably collect gas exhaled from the airways and gas aspirated from (or insuflated to) from the secluded nasal airways in series as well as unilateral nasal airways.

Preferred embodiments of the present invention will now be described herein below by way of example only with reference to the accompanying drawings, in which:

FIG. 1: Shows the basic anatomy of the upper respiratory tract.

Figure 2:
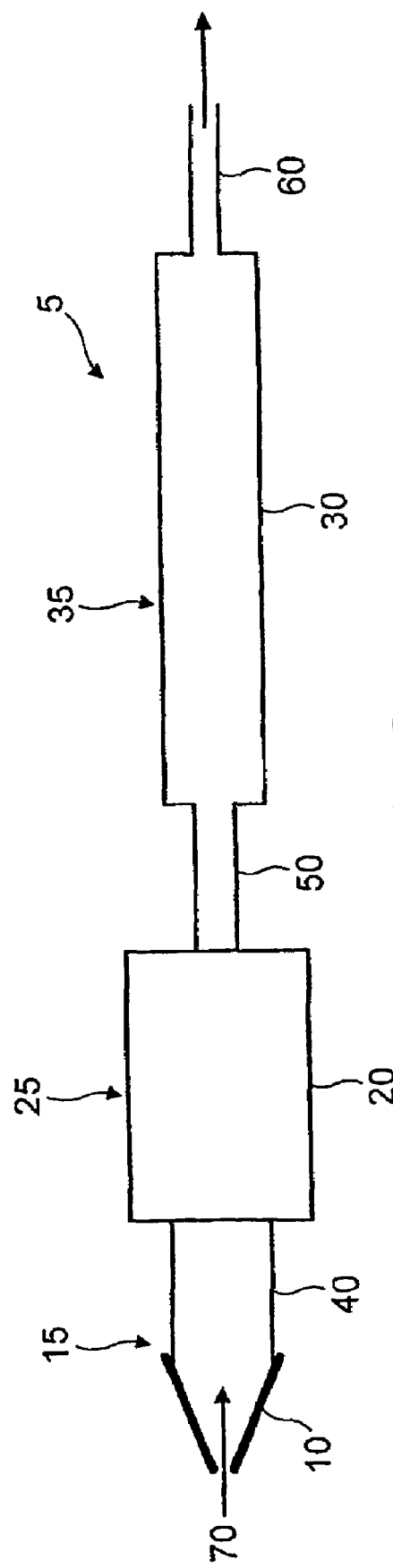

FIG. 2: Presents a apparatus according to the invention.

Figure 3A:
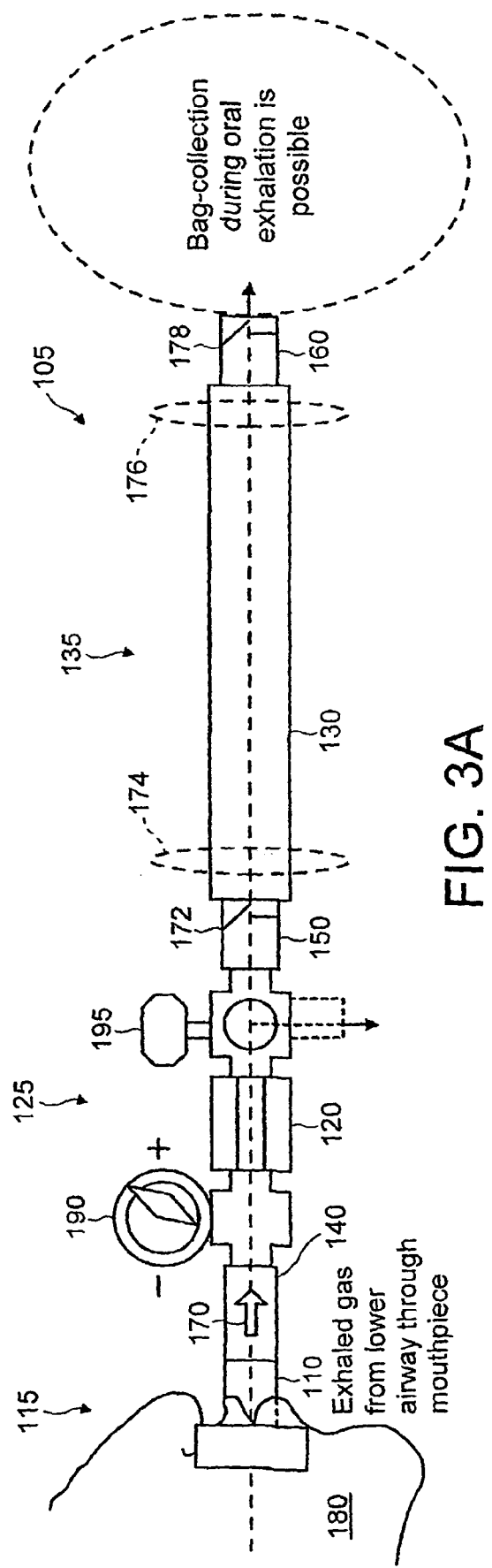
Figure 3B:
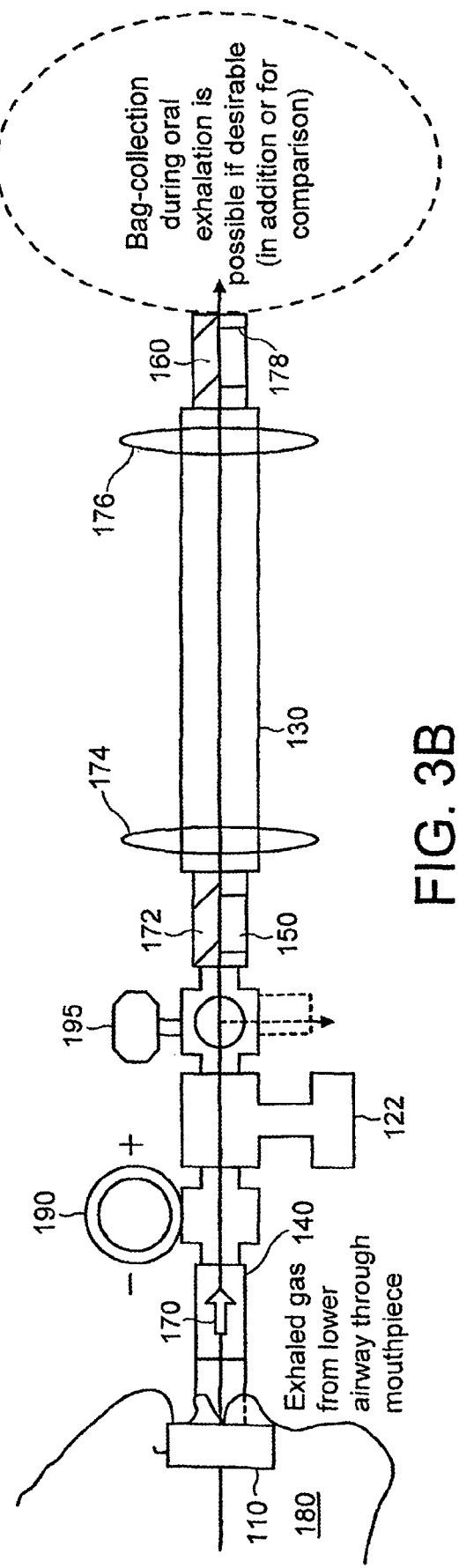

FIGS. 3A and 3B: Show Off-line collection of exhaled gases.

Figure 4A:
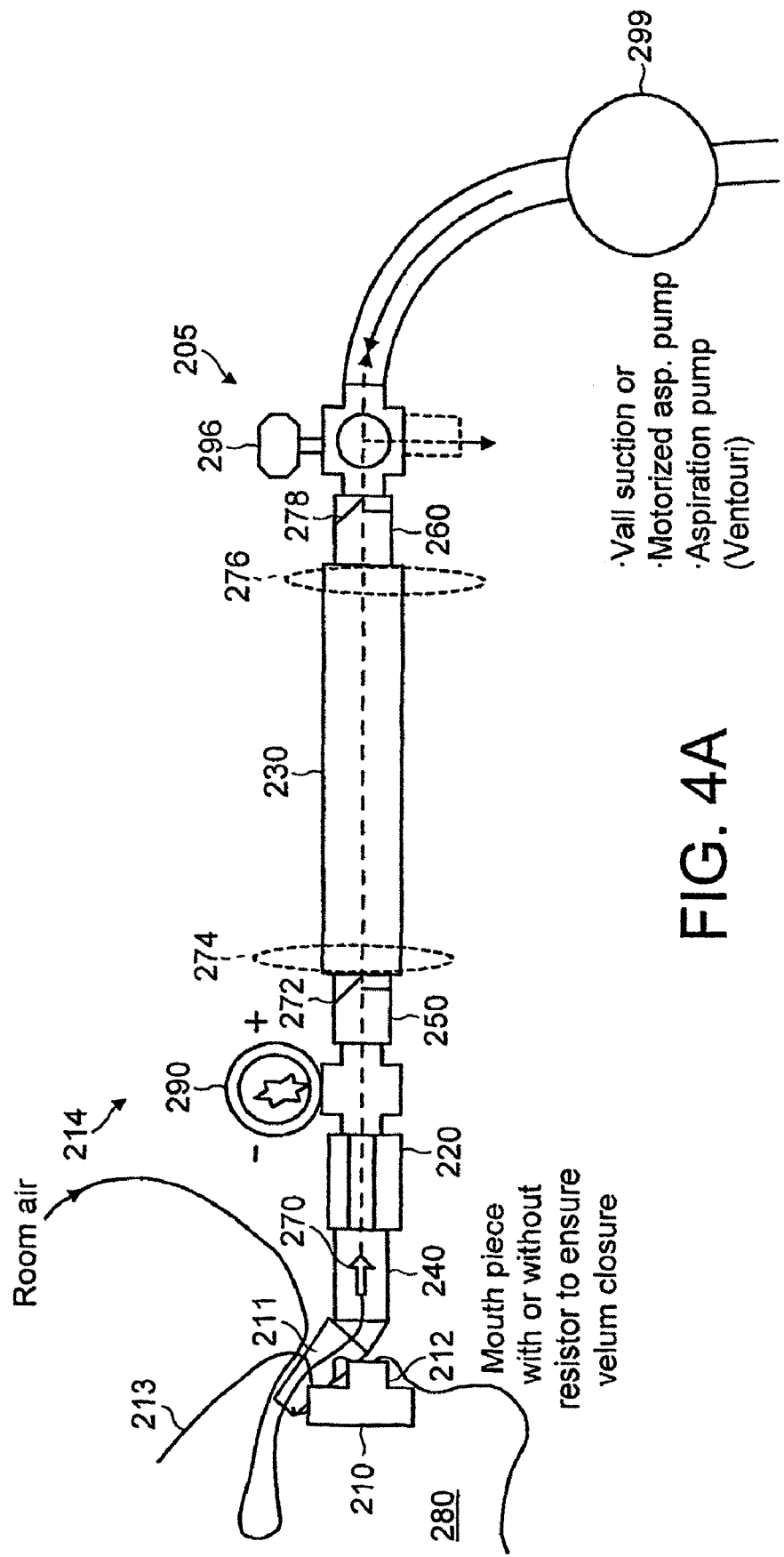
Figure 4B:
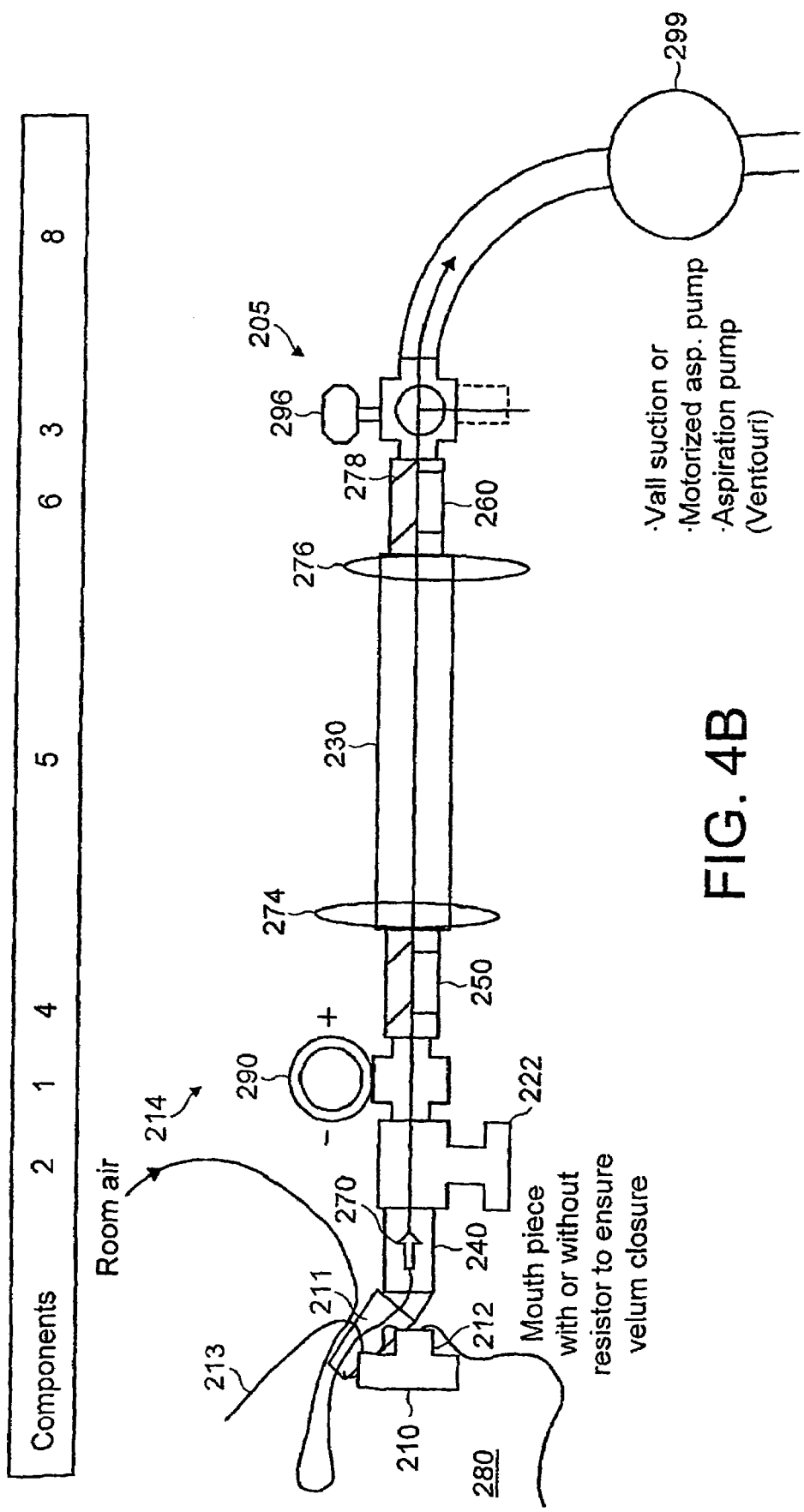

FIGS. 4A and 4B: Show Remote (off-line) collection of gases from the nasal airway FIGS. 5A and 5B: Show Simultaneous NO collection from lower airways and nasal cavites in series by insufflation technique FIGS. 5C and 5D: Show Simultaneous NO collection from the nasal cavites in series FIG. 6: Shows Exhaled Breath condensate collection FIG. 7: Shows Off-line collection of nasal condensate FIG. 8: Shows Lateral and Plan views FIG. 9: Shows a Graph of Correlation On-line vs Off-line NO conc. (ENO at 6,8 and 10 L/min 90 pairs of observation) and nasal aspiration at flows 5-8 L/min, (ENO at 6,8 and 10 L/min, 120 pairs of observation).

Figure 10:
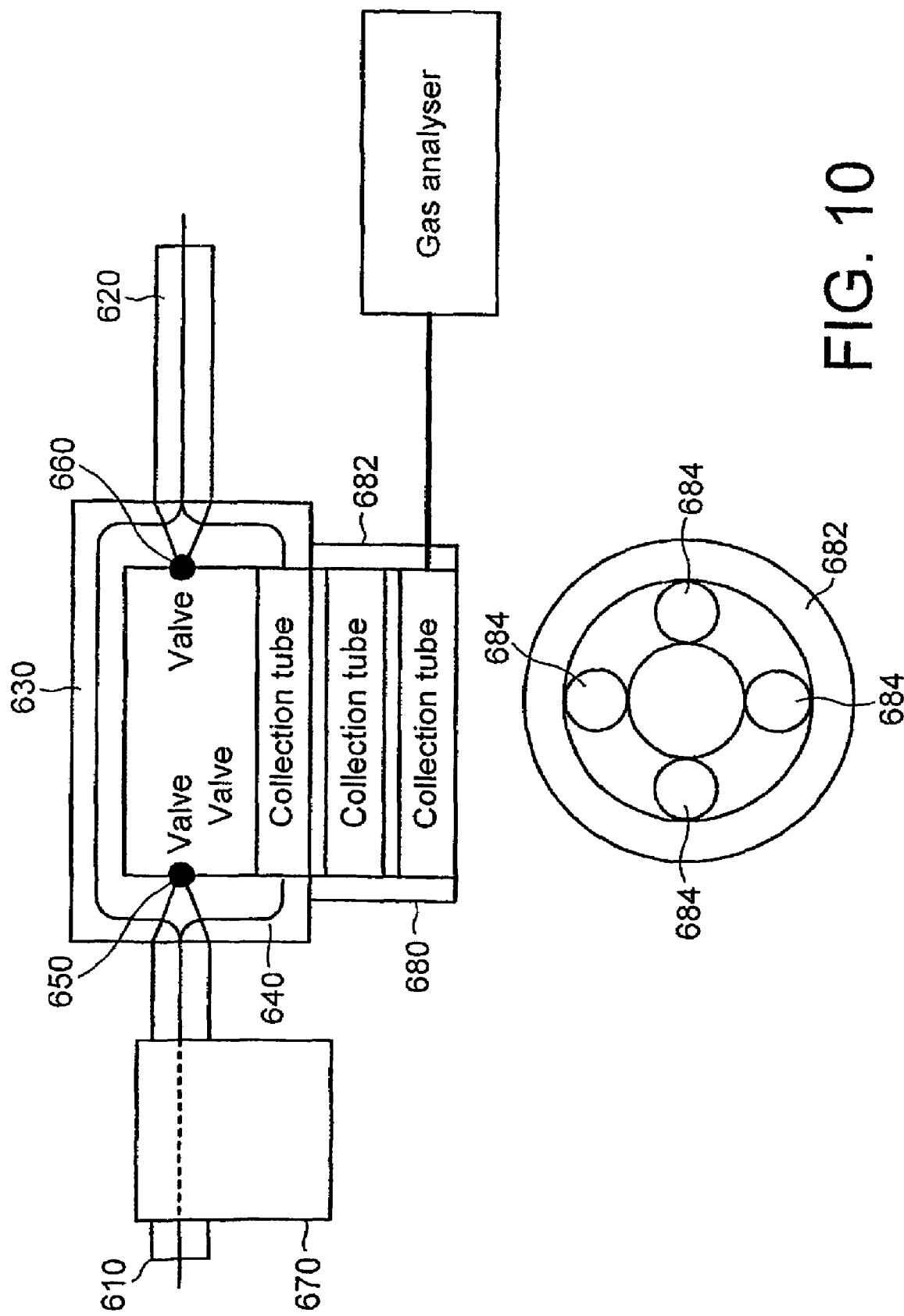

FIG. 10: Shows an apparatus for collecting gaseous samples during the respiratory cycle of a subject.

GAS COLLECTION NASAL AIRWAYS—ASPIRATION OR INSUFFLATION

The aspiration or insufflation may be provided by any one or more of: a mechanical device, an electrical pump or by the use of a syringe-like device permitting creation of a constant flow of 6 L/min for at least 20 seconds (ie a 2-3 L volume) aspiration, or by wall suction, a Venturi (aspiration) pump.

A preferred embodiment allows simultaneous flow controlled collection of gas exhaled from the lower airways and gas collected from the nasal airways after auto-insufflation.

Preferably, the subject exhales against a resistor. In this respect, air exhaled from the lower airways against a resistor is preferably at a fixed flow and is at a level that secures a closed velum. In addition, the exhaled same air can be used to flush (insufflate) the nasal airways. This method eliminates the need for an external pump or aspiration device and collection and analysis of gas concentration in room air becomes obsolete. The use of this method is most suitable for gases—such as NO—where the concentration entering the nasal airways is added to the net NO produced by the nasal airway (NO-output).

Collection of Condensate from Lower and Nasal Airways—Flow Controlled

Furthermore, the apparatus of the present invention can (such as after modification of the reservoir as described herein) be used for flow-controlled collection of condensate from the lower airways as well as the nasal airways without risk of contamination from other parts of the airway.

Reservoir for Collection of Exhaled, Aspirated an Insufflated Gas

An apparatus (5) for collection of exhaled gas form the lower airway is shown in FIG. 2.

In this respect, a mouthpiece (10) is connected to an adjustable/changeable resistor (20) optionally followed by a pressure gauge (not shown) with a measuring range of for example ±30 cm $H_2O$. These components may be connected with a tube-shaped gas collection reservoir (30) which has a one-way valve in each end (not shown) allowing air to pass only in one direction from the subject. The distal one-way valve may be connected to a mechanical three-way valve (not shown). The tube shape is chosen to reduce the risk of uneven distribution of flow and thus gas concentration. Such shapes are known to a person skilled in the art.

Different resistors with dimensions suited to produce the desired flows at the same positive pressure gradient are useful for avoidance of possible pressure related changes in NO output. The magnitude of this pressure sufficient to secure velum closure which is desired to prevent contamination of NO from the nasopharynx.

Procedure During Exhalation

The subject is instructed to take a deep breath and exhale while observing the pressure gauge and trying to keep a stable pressure corresponding to the desired flow, depending on the resistor used. After a standardised time (such as 10-15 seconds, depending on the flow used) the operator uses the three-way valve switch to abruptly redirect the airflow and thereby trapping a segment of the air in the reservoir between the one-way valves. In this way the problem of dead space is eliminated completely and the measurement repeated without introducing additional dead space.

Nasal NO-Measurements

Preferably, the same components described above for exhaled nitric oxide (ENO) measurements are used for collection of air aspirated from the nasal airway, but in a rearranged order (FIG. 4). The mouthpiece is replaced by a nasal olive (211) and the three-way valve (296) is relocated to a position after the reservoir (230) and the two one-way valves (272, 278). Finally, the order of the pressure gauge (290) and the resistor (220) was switched, since the air is aspirated and not blown into the reservoir. Aspiration was provided by wall suction, but any type of pump or other suitable means able to maintain a stable flow in the desired range can be used. Such means will be known by those skilled in the art.

The flow may be controlled by the degree of negative pressure, or by changing resistors, or by a flowmeter attached to the distal end of the apparatus as shown in FIG. 4, or by any combination, or other suitable means known to one skilled in the art.

Procedure Nasal Aspiration

The subjects are instructed to take a deep inspiration and hold their breath by doing oral Valsalva to maintain a closed velum. The nozzle was positioned to the subject's left nostril, and the room air or clean medical air <<zero gas>> is aspirated through nasal airway in series for 15 seconds. Again the three-way valve can be turned so that room air can be sucked in. A segment of the aspiration nasal air is thereby trapped in the reservoir. If room air is used the concentration of the measured gas must be recorded and its concentration subtracted before calculation of the output is performed (provided subtraction has been shown to be valid for the particular gas in the concentration in question).

Simultaneous Lower Airway Exhalation and Auto-Insufflation of Nasal Airways

The first part of the apparatus is as described as for exhalation from lower airways (as shown in FIG. 2). Instead of letting the exhaled air escape to the room, a tube is attached to the distal end and the flow controlled airstream is directed into one nostril via a tight fitting nasal olive (FIG. 5). The positive pressure inside the oral cavity is of a magnitude sufficient to secure a closed velum separating the oropharyngeal and the nasal airways. Only in rare cases of extremely high nasal resistance, will the positive pressure inside the nasal passage increase to the same level as the oropharyngeal pressure and thereby jeopardize the velum closure. This risk is reduced by applying the nasal insufflation olive to the less patent nostril. Another nasal olive attached to another reservoir with one-way valves each end (see below) is introduced to the second nostril, and the air from the nasal airways is collected in series. Exhaled oral gas concentration is thus subtracted from the nasal gas concentration and both values are obtained in the same procedure without need for external pumps.

The Reservoir for Gas Collection

The tube shaped open design of the reservoir enables the air inside to be readily flushed through. When the three-way valve is switched, the representative gas sample is trapped within the tube. The volume of the tube is adjusted according to the requirement of the analyzer available and to the flow used. The volume should be large enough to include several of the oscillations in flow above and below the intended flow. At a flow of 6 L/min (100 ml/sec), a reservoir of 200 ml representing 2 seconds of exhalation or aspiration seems adequate to cancel out effects of such oscillations and thus provide a value representative of an average flow of the intended flow.

Depending on the properties of the gas, duration between collection and analysis and transport conditions different materials can be used. If flexible compressible tubes fulfil the given requirement and conditions, clamps can be used (or applied) to seal off the tube before detachment from the collection apparatus. Collection can subsequently be done by penetrating the plastic with a needle. A needle is introduced in the opposite side to prevent negative pressure to impact the sampling flow. This is a preferred embodiment of the present invention.

If long duration storage is required or the properties of the gas are such that suitable flexible tubing is not available, reusable collection reservoirs with two additional valves within the reservoir itself can be used.

Collection of Condensate

The same set-ups described above are used, but the reservoir is changed to allow maximum condensation of fluid with its soluble substances to condense. This is achieved by using a coil of tubing or reservoir (plastic bag) with a large surface and by immediate cooling. This can easily be done by immersing this reservoir into an ice bath, or any other suitable cooling device. The flow can be controlled both when sampling from the lower airways and when aspirating from the secluded nasal airway. The accumulated amount of condensate can exceed the volume obtained by the instant freezing method (Cryocond) and the fluid can easily be transferred to a storage container for analysis or freezing for later analysis.

The apparatus of the present invention is a new and useful apparatus for the remote collection of gases and condensates from the airways. This type of examination is gaining increasing interest in research, but more important for clinical purposes in diagnostics and monitoring of airway diseases (and potentially other diseases, gastroenterologic diseases such as gastric ulcer, liver, kidney disease). The apparatus itself may include flow control and/or valve systems. Furthermore, different types of reservoirs (disposable or reusable) may be used for collection and storage of gases and condensates.

Collection of Gases from the Lower Airways

The prior art methods developed for collection of gases from the lower airways in bags are unsatisfactory, since they do not completely eliminate the problem of the dead-space. This applies to dead-spaces in the upper airways, the sampling device with connections, as well as the sampling bag. Collection of exhaled air during tidal breathing is unsatisfactory, due to the unknown impact of variation of dead-space and changing flow-rate.

In contrast, an active single breath exhalation at a constant flow and pressure with the apparatus and method of the present invention is employed to eliminate the pressure and flow dependence of gas concentrations and output (ie. concentration multiplied by flow). Exhalation at a constant positive pressure of sufficient magnitude is used to secure velopharyngeal closure, and thus prevent contamination of gases in the nasal and paranasal airways.

Collection of Gases from the Nasal Airway

Aspiration of nasal air from the nasal cavities in series during a constant positive pressure in the oral cavity securing a closed velum is a preferred technique of collection of nasal gas in accordance with the present invention. If severe congestion impedes the use of aspiration flows of sufficient magnitude, the present invention provides for insufflation through the nasal passages in series. This method requires that gas is aspirated by a pump or any suitable suction device at a constant flow. To obtain the true gas concentration (and calculated output) originating from the nasal airway, the concentration of the particular gas in room air may be subtracted (Qian et al). Room air is collected separately and analyzed together with the gas collected from the nose. Alternatively, so called 'zero-gas' can be aspirated or insufflated.

The apparatus of the present invention is advantageous over the prior art devices since there is no need for a compressible deflatable bag which can be completely emptied, restricts the type and thickness of the material used. In addition with the prior art devices, it was often the case that unsatisfactory single breaths expiration were obtained thus making complete emptying of the bag difficult. This problem does not arise with the apparatus of the present invention. Also, with the prior art devices, if they are reused, an potential additional dead-space is introduced and cleaning is impossible. This problem does not arise with the apparatus of the present invention. Also, with the prior art devices, the bag collection methods are not suitable for collection of nasal gas during aspiration not for collection of condensate. This problem does not arise with the apparatus of the present invention.

Moreover with some prior art devices, instant freezing of exhaled air during tidal breathing is used to collect condensate for later analysis. The flow dependence of substances in the condensate as well as potential contamination from the upper or lower airways respectively reduces the reproducibility and reliability of collection during tidal breathing. Furthermore, instant freezing requires a special apparatus adding cost and complexity to the collection. These problems do not arise with the apparatus of the present invention.

The present invention enables reliable measurement of exhaled gases and gases from the nasal airways by providing control of the flow rate and/or pressure. In particular, the flow rate and the pressure (positive for exhalation and negative for aspiration) can influence the release of gases from the mucosa of the nasal airways. It is therefore important to be able to be able to control both the flow rate and the pressure, particularly to maintain a stable flow rate or pressure where the other of the flow rate or pressure can vary. Thus, the present invention enables the use of flow meters based on other than flow resistors, such as temperature change, propellor rotation and a rotatmeter (ball inside a glass tube), to calculate the gas output (i.e. gas concentration flow) at fixed flow.

Practical Testing of Apparatus Types

These studies confirm the improved distribution and good tolerability provided for by the apparatus of the present invention. In particular, the combined exhaled, nasal apparatus simplifies remote collection considerably.

Gas or condensate collection according to the invention may be advantageously conducted at constant pressures/ constant flow rates. The possibility of standardizing parameters, for example the flow and/or pressure and/or timing and/or duration, of the gas or condensate collection is an advantageous feature of the present invention which may preferably improve the reproducibility and/or reliability of this type of collection/diagnostic procedure.

A study has been performed in 10 subjects using three different flow for exhaled gas (NO-analysis) and for nasal aspiration. Prototype testing of the new apparatus has been carried out.

The apparatus can be assembled from parts which to a large extent exist commercially available. The combined exhaled and nasal collection system functions properly in practice.

The provided gas and condensate analysis methods can be used as a non-invasive diagnostic tool and in home monitoring of airway diseases and other types of diseases. Chronic airway disease is very common and the incidence increasing. This invention is also very useful for evaluation the impact of environmental exposures and the results of interventions which are of increasing interest. The non-invasive nature of these methods is very advantageous and they may prove to be very useful and expand rapidly in the future.

FIG. 2 presents an apparatus (5) according to the invention. This comprises a first component (15) which is essentially a connection means for connecting the apparatus (5) to the patient (not shown). In addition, the apparatus (5) comprises a second component (15) which is essentially a resistance means for providing a resistance to airflow from the patient. The third component (35) is essentially a containment means for containing a volume of gas.

In more detail, the first component (15) comprises a mouthpiece 10 which can be placed between the subject's lips (not shown). In addition, the first component (15) has a tube (40) onto one end of which the mouthpiece is connected. The mouthpiece (10) can be connected to the tube (40) by any suitable means, such as by interference fit, by a screw fit arrangement, by a snap-fit arrangement. Alternatively, the mouthpiece (10) can be integral with the tube (40).

The second component (25) comprises a resistor (20). This resistor (20) is connected to the tube (40) of the first component such that gases exhaled into the mouthpiece (10) are directed into the resistor. In addition, the second component (25) has a tube (50) which is connected to the resistor (20) at the end distal from the connection to the first component (15).

The third component (35) of the apparatus (5) comprises a tubular collection reservoir (30). This is connected to the tube (50) of the second component in such a way that gases leaving the resistor (20) are channelled into the collector (30). The third component also has a tube (60) which is connected to the end of the collection resevoir (30) distal from the second component (25).

In use, a subject places the mouthpiece (10) in between his/her lips, and exhales into the first component (15) of the apparatus (5). Gases exhaled by the subject (70) pass into the mouthpiece (10), through the tube (40) and into the resistor (20). As the gases are not able to freely escape from the resistor (20), a resisitance is set up such that the velum (see FIG. 1) closes. As indicated above, our research has shown that a positive pressure equivalent to about 10 cm $H_2O$ is sufficient to keep the soft palate velum closed. In addition, our research has shown that a subject would normally be able to maintain a flow rate of about 3-15 liters per minute for at least about 10-20 seconds.

After exiting the resistor, the gases pass through another tube (50) and into the collection resevoir tube (30). Finally, the gases pass out of the collection resevoir tube (30) through a connecting tube (60). Here the gases may be directed into the room air, or into further apparatus (see below).

One of the advantageous features of this invention is that there is extremely limited dead space in the apparatus. The flow of gases through the apparatus flushes out room air or whatever gases might have been present before sample collection begins, such as medical 'zero gas'. The positive pressure generated by exhalation against the resistor ensures that the velum is closed, and thereby avoids contamination of lower airway gases with nasal gases, or vice versa. This feature allows simultaneous collection of nasal and lower airway gases, either seperately or in series (as described below).

Another advantageous feature is that a preferred collection resevoir is in the form of a tube. This tube may be sealed once collection is complete by clamping of the ends with any suitable mechanical clamping means such as jubilee clips, thumbscrew closures or spring-clips. Alternatively, sealing valves may be used which can simply be closed after the collection is complete.

FIG. 3A shows an alternative apparatus 105 according to the invention. In this embodiment the subject 180 exhales into a mouthpiece 110, which exhaled gases 170 then pass into a tube 140, through a pressure gauge 190, and into a resistor 120 which ensures closure of the velum on exhalation by the subject through the mouthpiece. The gases then exit the resistor 120 through a three-way valve 195, through a tube 150, through a one-way valve 172 and into the gas collection reservoir tube 130. The gases may then exit the collection tube 130 by way of another tube 160 with a one-way valve 176, and into the atmosphere, be collected in a bag, or channelled into another apparatus (for example see below). Once collection is complete, the gases may be sealed into the collection tube 130 by clamping the ends of the tube 130 with suitable means such as clamps 174, 176 or valves (eg 195).

FIG. 3B shows another alternative apparatus 105 according to the invention; this apparatus being a modification of the apparatus of FIG. 3A. In this embodiment the subject 180 exhales into a mouthpiece 110, which exhaled gases 170 then pass into a tube 140, through a pressure gauge 190, and into a flow meter 122 which ensures closure of the velum on exhalation by the subject through the mouthpiece and controls the flow rate. The gases then exit the flow meter 122 through a three-way valve 195, through a tube 150, through a one-way valve 172 and into the gas collection reservoir tube 130. The gases may then exit the collection tube 130 by way of another tube 160 with a one-way valve 178, and into the atmosphere, be collected in a bag, or channelled into another apparatus (for example see below). Once collection is complete, the gases may be sealed into the collection tube 130 by clamping the ends of the tube 130 with suitable means such as clamps 174, 176 or valves (eg 195).

FIG. 4A shows an alternative apparatus 205 according to the invention. In this embodiment the subject 280 exhales into a mouthpiece 210 which contains a resistor 212 to ensure velum closure. The gases from the mouthpiece 210 and the resistor 212 may escape into the atmosphere, or may be collected. In this embodiment the gases are allowed to escape into the atmosphere. A nasal olive 211 is located in one of the nostrils 213 of the subject 280. While the subject 280 exhales against the resistor 212, ensuring velum closure, room air 214 is aspirated through the nasal passage, entering through the other, free nostril (not shown), and exiting via the nasal olive 211 in the one nostril 213. The nasal gases 270 are drawn through a tube 240, a resistor 220, a pressure gauge 290, a tube 250 and are collected in a tubular gas reservoir 230. The reservoir 230 may be sealed once collection is complete by way of clamps 274, 276 or valves eg 296. The aspiration of the nasal gases may be performed by any suitable means, such as a pump 299 or by suction.

FIG. 4B shows an alternative apparatus 205 according to the invention; this apparatus being a modification of the apparatus of FIG. 4A. In this embodiment the subject 280 exhales into a mouthpiece 210 which contains a resistor 212 to ensure velum closure. The gases from the mouthpiece 210 and the resistor 212 may escape into the atmosphere, or may be collected. In this embodiment the gases are allowed to escape into the atmosphere. A nasal olive 211 is located in one of the nostrils 213 of the subject 280. While the subject 280 exhales against the resistor 212, ensuring velum closure, room air 214 is aspirated through the nasal passage, entering through the other, free nostril (not shown), and exiting via the nasal olive 211 in the one nostril 213. The nasal gases 270 are drawn through a tube 240, a flow meter 222 which controls the flow rate of the aspirated nasal gases, a pressure gauge 290, a tube 250 and are collected in a tubular gas reservoir 230. The reservoir 230 may be sealed once collection is complete by way of clamps 274, 276 or valves eg 296. The aspiration of the nasal gases may be performed by any suitable means, such as a pump 299 or by suction.

Ensuring closure of the velum by the resistive arrangement prevents contamination of the nasal gases collected in this manner, and as such is an advantageous feature of the current invention.

The exclusion of gases or other substances from the lower airways and/or the oral/buccal cavity during nasal gas collection may advantageously improve the specificity of the collection of substances (gases) originating from the nasal passages. In this way, nasal gases collected according to the invention may preferably be kept substantially free of gases originating from the lower airways or oral/buccal cavities. Advantageously, nasal gases collected according to the invention are not contaminated with gases from other airways, cavities or parts of the subject's respiratory tract(s). This is an advantageous feature of the current invention.

Figure 5A:
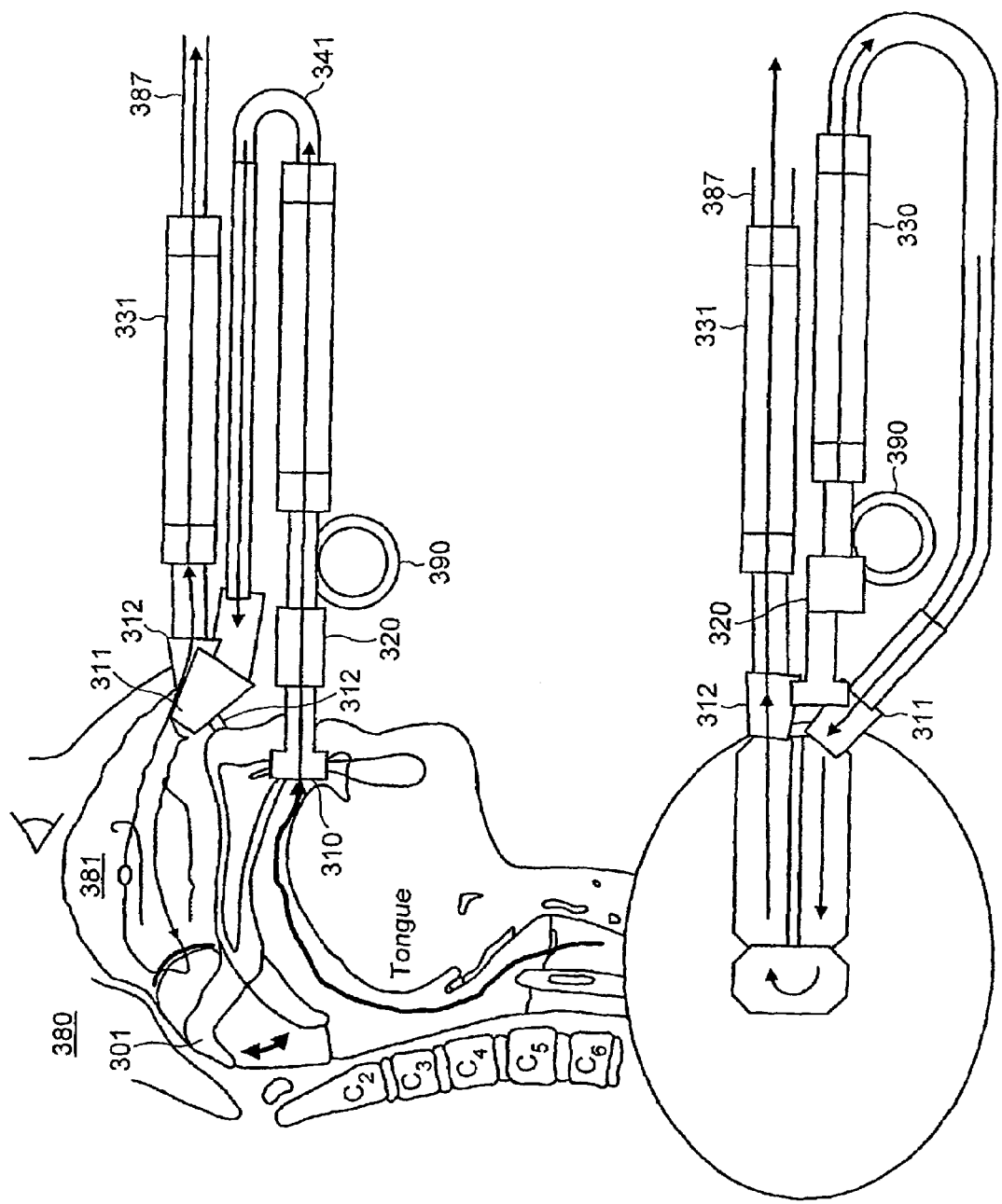

In FIG. 5A, an alternative apparatus according to the invention is presented. Here, the subject 380 exhales through a mouthpiece 310 and a tube 340 directs the exhaled gases through a resistor 320 which ensures the velum 301 is closed. The gases then pass through a pressure gauge 390 and into a collection reservoir 330, through a tube 341, a nasal olive 311 inserted into one of the subject's nostrils and into the nasal cavity 381 of the subject 380. The gases then travel through the nasal cavity 381 and egress through the other nostril into which a second nasal olive 312 has been inserted. The gases exiting via this second nasal olive 312 then pass into a second collection reservoir 331, and into the atmosphere through a tube 387. The gases may instead be collected from this tube 387, or may pass through further apparatus, for example, a condenser (not shown). The collection reservoirs may be sealed as in examples 3 or 4 (FIG. 3, FIG. 4).

Figure 5B:
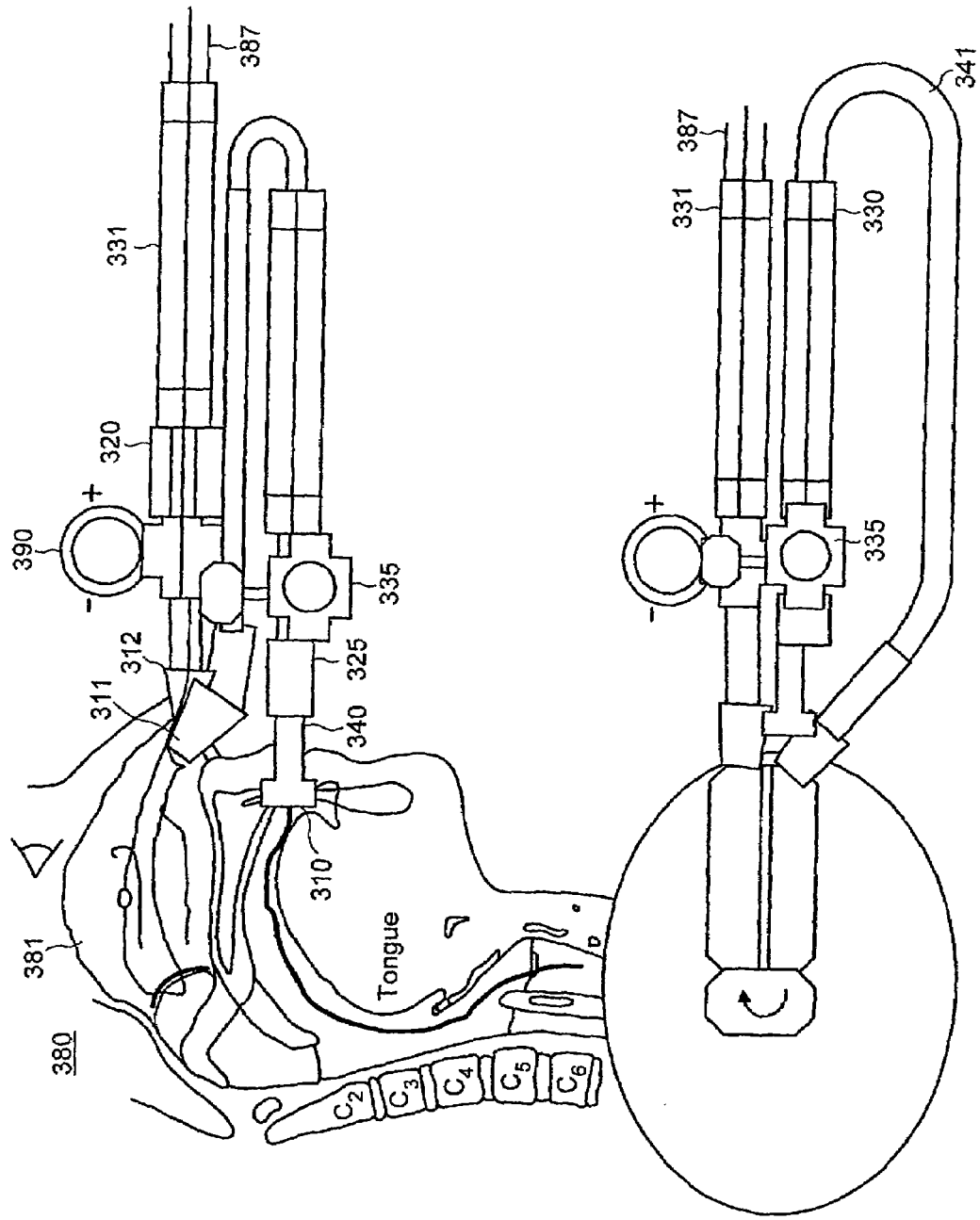

FIG. 5B illustrates another alternative apparatus according to the invention; this apparatus being a modification of the apparatus of FIG. 5A. Here, the subject 380 exhales through a mouthpiece 310, which exhaled gases are directed through a tube 340, a filter 325, a three-way valve 335, into a collection reservoir 330, through a tube 341, a nasal olive 311 inserted into one of the nostrils of the subject and into the nasal cavity 381 of the subject 380. The gases then travel through the nasal cavity 381 and egress through the other nostril into which a second nasal olive 312 has been inserted. The gases exiting via this second nasal olive 312 then pass through a pressure gauge 390, a flow resistor 320 which regulates the flow rate and pressure in the nasal cavity 381, into a second collection reservoir 331, and into the atmosphere through a tube 387. In this embodiment, by providing the pressure gauge 390 upstream of the flow resistor 320, it is possible to measure the combined resistance of the nasal passages in series. The gases may instead be collected from the tube 387, or may pass through further apparatus, for example, a condenser (not shown). The collection reservoirs may be sealed as in examples 3 or 4 (FIG. 3, FIG. 4).

Figure 5C:
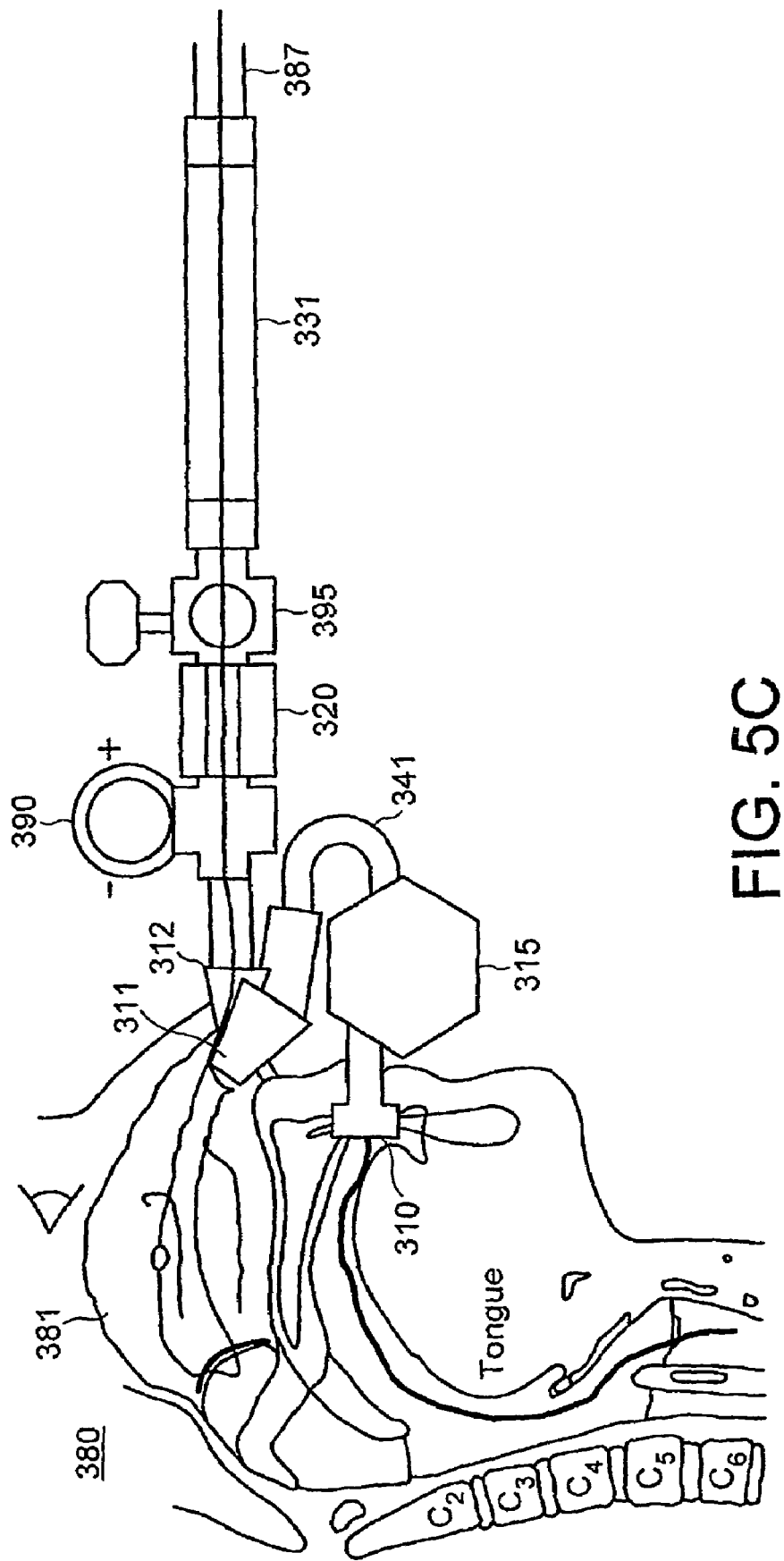

FIG. 5C illustrates yet another alternative apparatus according to the invention; this apparatus being a modification of the apparatus of FIG. 3A. Here, the subject 380 exhales through a mouthpiece 310, which exhaled gases are directed through a scrubber 315 for removing NO or other gases of interest from the exhaled gases, a tube 341, a nasal olive 311 inserted into one of the nostrils of the subject and into the nasal cavity 381 of the 15 subject 380. In another embodiment a moisture and/or anti-microbial filter may be included downstream of the mouthpiece 310. The gases then travel through the nasal cavity 381 and egress through the other nostril into which a second nasal olive 312 has been inserted. The gases exiting via this second nasal olive 312 then pass through a pressure gauge 390, a flow resistor 320 which regulates the flow rate and pressure in the nasal cavity 381, through a three-way valve 395, into a second collection reservoir 331, and into the atmosphere through a tube 387. In this embodiment, by providing the pressure gauge 390 upstream of the flow resistor 320, it is possible to measure the combined resistance of the nasal passages in series. The gases may instead be collected from the tube 387, or may pass through further apparatus, for example, a condenser (not shown). The collection reservoirs may be sealed as in examples 3 or 4 (FIG. 3, FIG. 4).

No external pump or suction device is required, and this embodiment is thus unique for field studies. This alternative is probably the most users friendly, because it may be a bit cumbersome to collect in two collections tubes simultaneously.

The determination of desired flow by a combination of resistor and pressure gauche may be replaced by a flowmeter of a rotameter type or similar. When collection nasal NO (alone with scrubber—or simultaneously with collection of ENO), the nasal airway will provide a variable resistance to airflow. Consequently, the pressure through the nasal passages in series may vary, making it unreliable to position the resistor/pressure gauche just after the scrubber. (However, if a flowmeter of a different design (lik a rotameter) is used, it may be placed just after the scrubber/moisture filter).

Figure 5D:
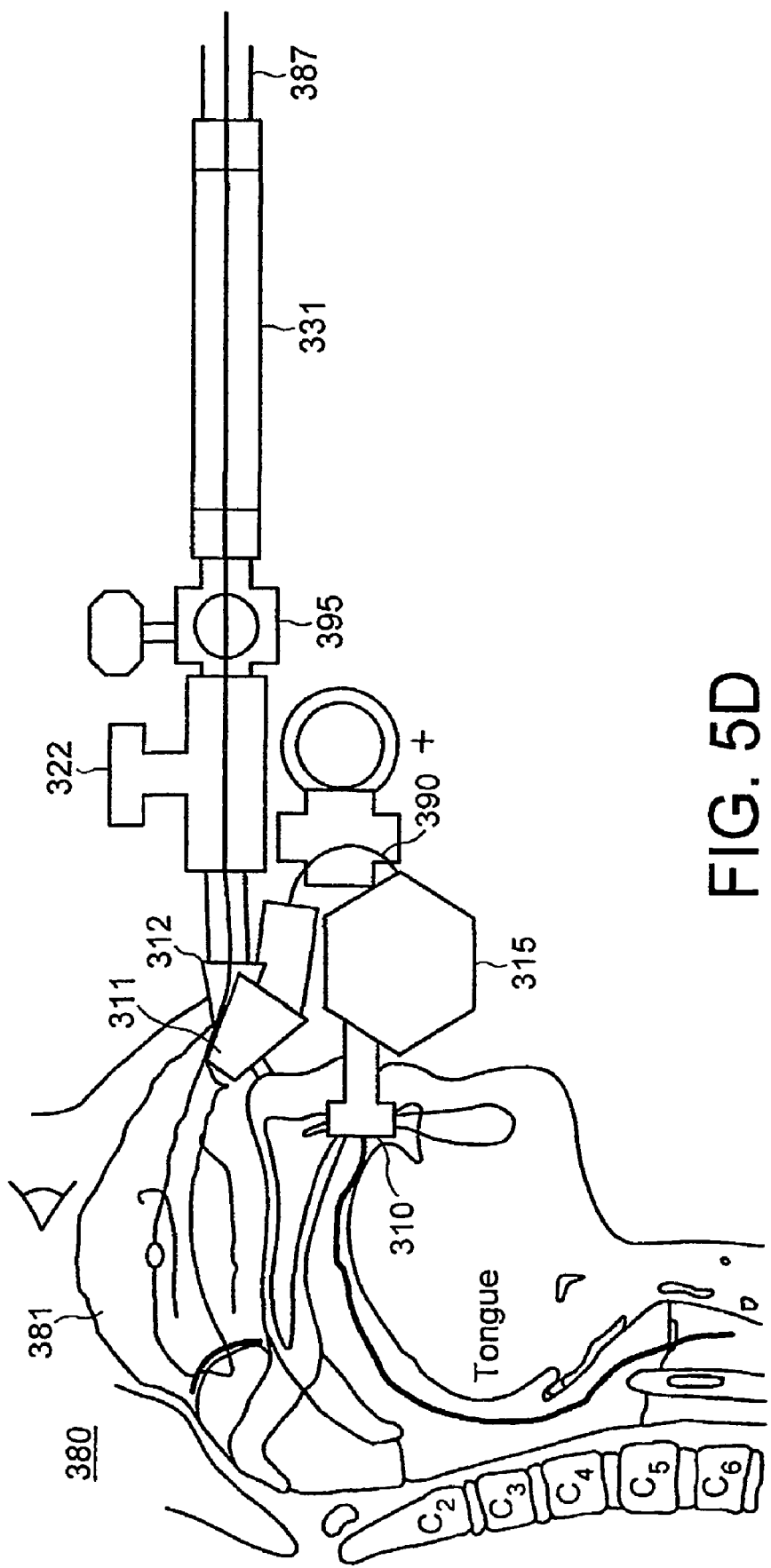

FIG. 5D illustrates yet another alternative apparatus according to the invention; this apparatus being a modification of the apparatus of FIG. 5A. Here, the subject 380 exhales through a mouthpiece 310, which exhaled gases are directed through a scrubber 315 for removing NO or other gases of interest from the exhaled gases, a pressure gauge 390, a nasal olive 311 inserted into one of the nostrils of the subject 380 and into the nasal cavity 381 of the subject 380. The gases then travel through the nasal cavity 381 and egress through the other nostril into which a second nasal olive 312 has been inserted. The gases exiting via this second nasal olive 312 then pass through a pressure gauge 390, a flow meter 322 which regulates the flow rate through the nasal cavity 381, through a three-way valve 395, into a second collection reservoir 331, and into the atmosphere through a tube 387. The gases may instead be collected from the tube 387, or may pass through further apparatus, for example, a condenser (not shown). The collection reservoirs may be sealed as in examples 3 or 4 (FIG. 3, FIG. 4).

With the apparatus of FIGS. 5A to 5D, the true nasal gas concentration can be measured directly. In FIGS. 5C and 5D, the scrubber 315 can be omitted, but then the concentration of the gases from the lungs has to be measured and subtracted from the concentration of the nasal gases.

The determination of desired flow by a combination of resistor and pressure gauche may be replaced by a flowmeter of a rotameter type or similar. When collecting nasal NO (alone with a scrubber—or simultaneously with collection of ENO, the nasal airway will provide a variable resistance to airflow. Consequently, the pressure through the nasal passages in series may vary, making it unreliable to position the resistor/pressure gauche just after the scrubber. (However, if a different design (like a rotameter) is used in may be placed just after the scrubber/moisture remover).

Figure 6:
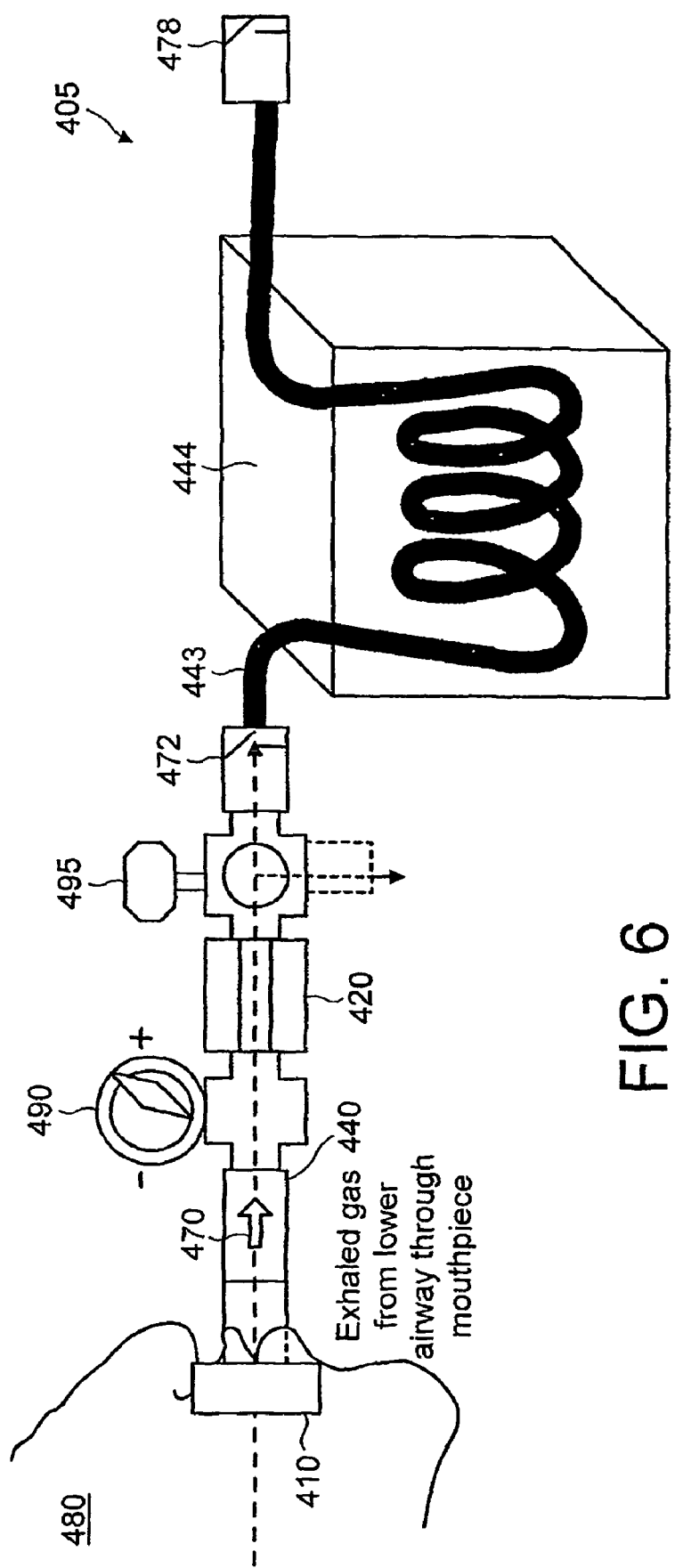

In FIG. 6, an alternative apparatus (405) according to the invention is presented. This apparatus (405) is for the collection of exhaled gas condensate. Here, the subject (480) exhales through the mouthpiece (410), causing exhaled gases (470) to pass through the tube (440) and into the pressure gauge (490), and into the resistor (420). This resistance leads to an increased pressure in the airways, ensuring velum closure (not shown). The gases then travel through a three-way valve (495), through a one-way valve (472), and into a collection tube (443). This collection tube is placed in a condensing apparatus (444) to promote efficient condensation of condensate from the exhaled gases. This condensing apparatus (444) may comprise a bucket of iced water, a refrigerated coolant such as polyethylene glycol, solid phase carbon dioxide or any other suitable means of cooling the tubular collection reservoir (443). Finally, the gases exit the apparatus via a tube with one-way valve (478).

Figure 7:
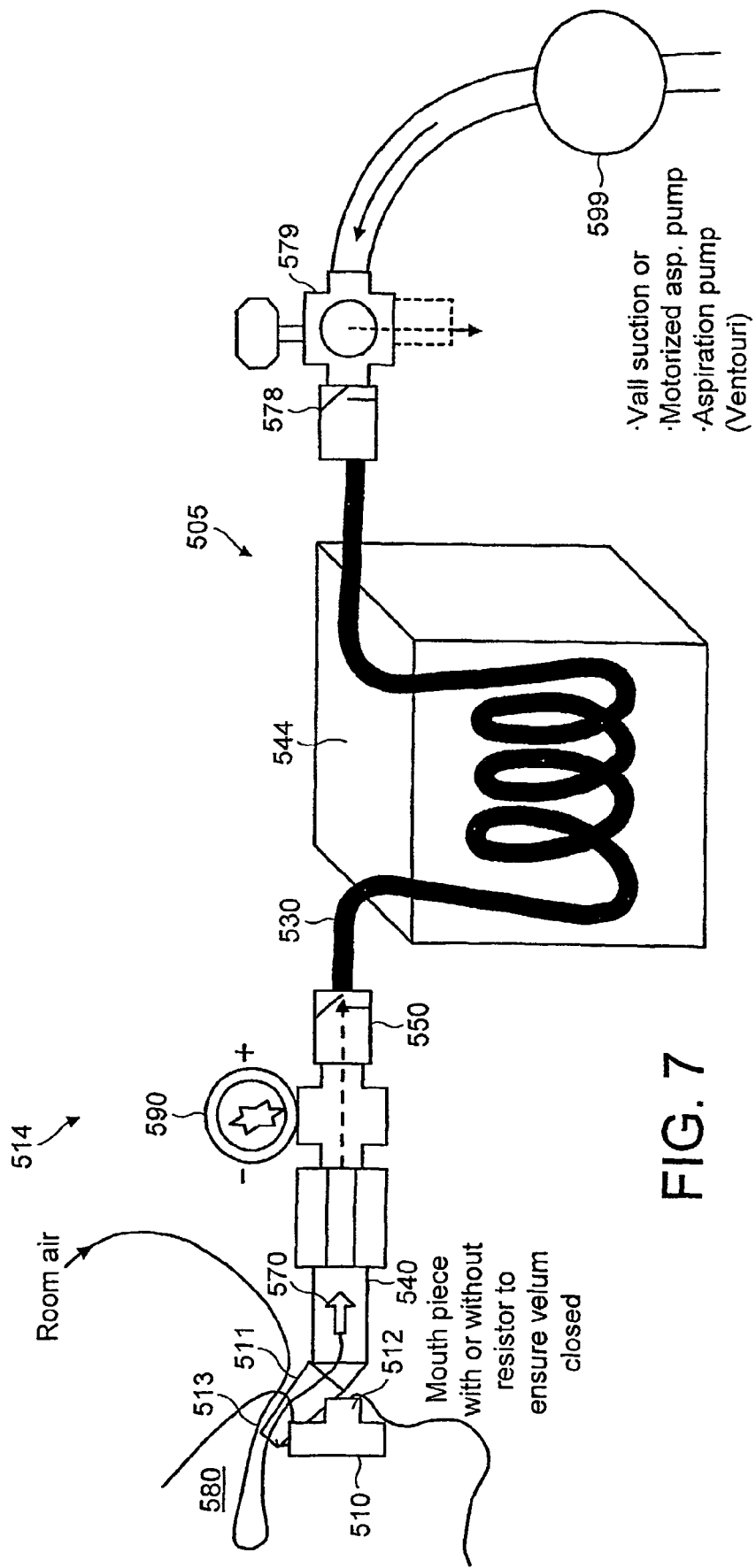

In FIG. 7, an alternative apparatus (505) according to the invention is presented. This apparatus (505) is for the collection of nasal gas condensate. Here, the subject (580) exhales through a mouthpiece (510), incorporating a resistor (512). This resistance leads to an increased pressure in the airways, ensuring velum closure (not shown). The gases from this mouthpiece (510) and resistor (512) may escape into the room, or may be collected. In this example, they are allowed to escape into the room. Simultaneously with exhalation through this mouthpiece (510), a nasal olive (511) is placed in one of the subject's nostrils (513). Whilst the subject exhales against the resistor (512), ensuring velum closure, room air (514) is aspirated through the subject's nasal passage, entering through the one free nostril (not shown), and exiting via the nasal olive (511) in the other nostril (513). These nasal gases (570) are drawn through a tube (540), a resistor (520), a pressure gauge (590), a tube (550) and pass through a tubular gas resevoir (530). This tubular collection resevoir (530) is placed in a condensing apparatus (544) to promote efficient condensation of condensate from the exhaled gases. This condensing apparatus (544) may comprise a bucket of iced water, a refrigerated coolant such as polyethylene glycol, solid phase carbon dioxide or any other suitable means of cooling the tubular collection resevoir (530). Finally, the gases exit the apparatus via a tube with one-way valve (578) and a three-way valve (579). The gases may be aspirated by any suitable means such as a pump (599) or by suction (not shown).

Figure 8:
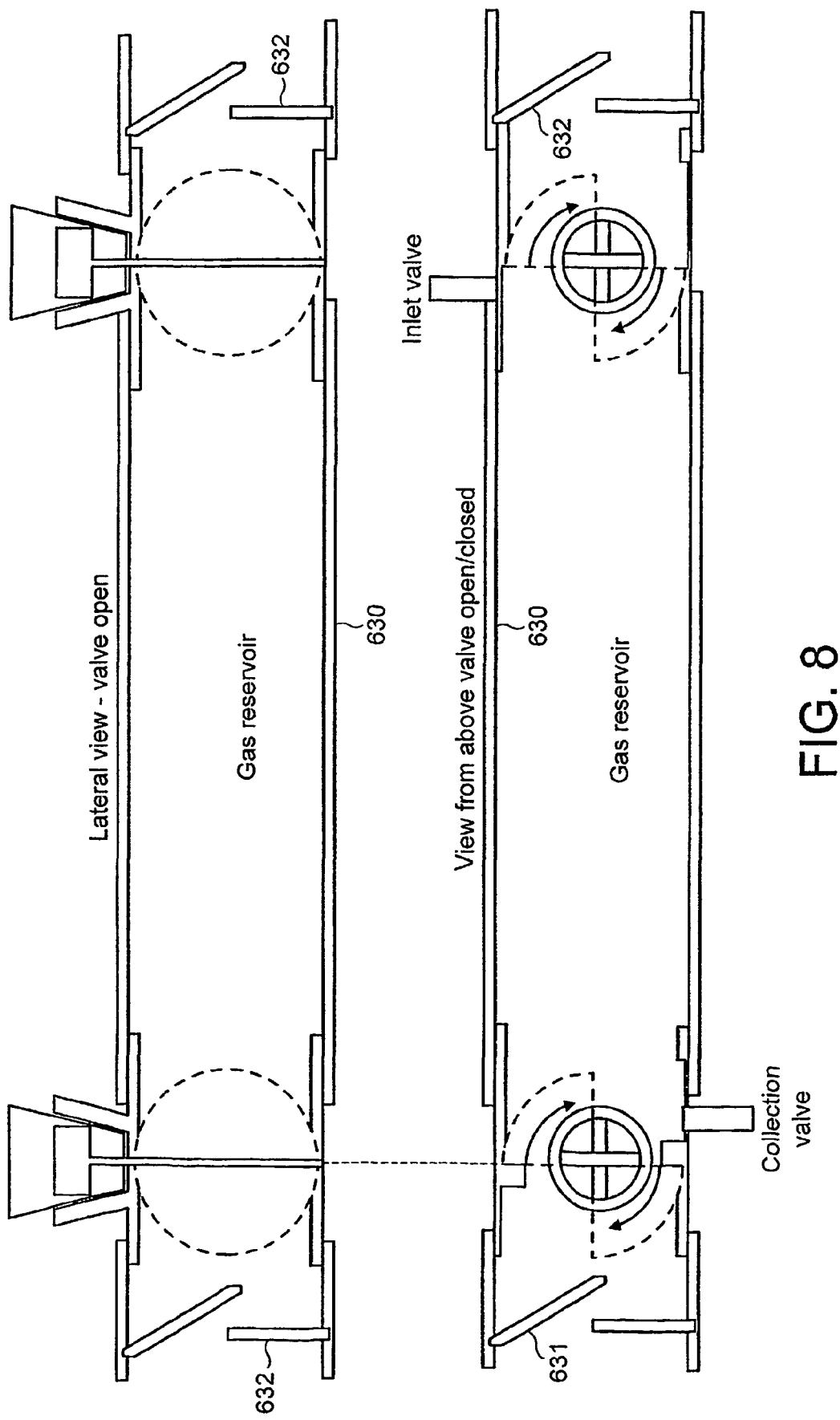
Figure 9:
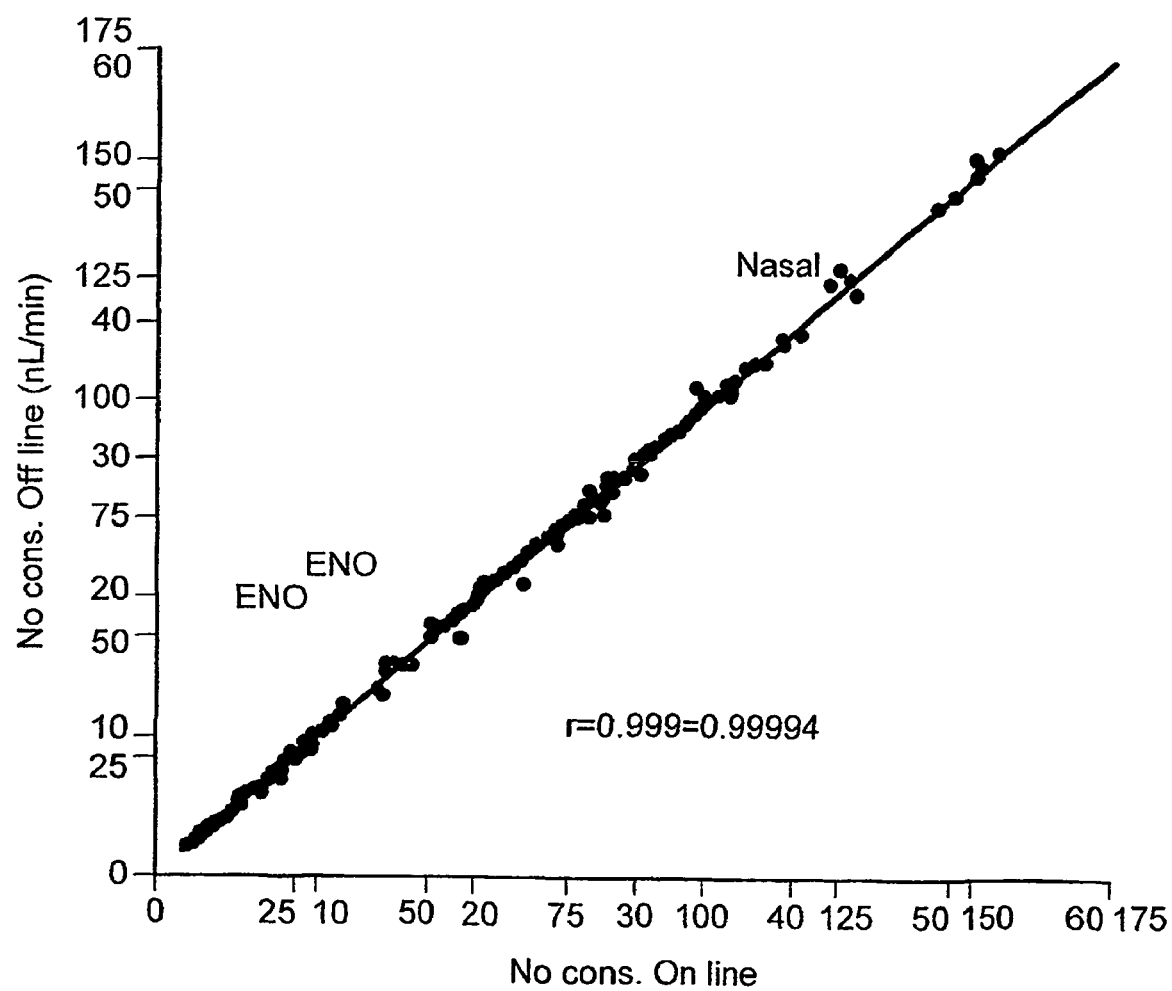

FIG. 8 shows lateral and plan views of a gas collection resevoir according to the invention. The gases may flow through the gas resevoir (630) in one direction only, flow in the opposite direction being restricted by one-way valves (631, 632).

The collection chambers or resevoirs for gases and/or condensate according to the invention may be advantageously coated with a material capable of absorbing or adsorbing or otherwise trapping certain substances such as gases, particles, or microorganisms for example bacteria or viruses, or parts thereof.

A device may preferably be incorporated into the apparatus according to the invention, said device being capable of adsorbing, absorbing or otherwise trapping certain substances such as gases, particles, or microorganisms for example bacteria or viruses, or parts thereof. Preferably, this device is a filter. Such a filter could be placed before, inside or after the collection chamber to absorb/trap said substances. Preferably, said filter would be removable.

Preferably, the coating or filter is designed in such a way as to allow rapid detection of the concentration (for example the prescence or abscence) of said substances.

The coating or the filter(s) may advantageously be made in such a way that on-site detection/diagnosis of the quality and/or quantity of absorbed substances is possible. The coated chamber of the collection device and/or filter(s) can advantageously be removed or stored for subsequent analysis.

FIG. 10 illustrates a gas collection device in accordance with a further embodiment of the present invention. This embodiment finds particular application in collecting gases from sleeping, anaesthetised or unconscious subjects.

The apparatus comprises a first port 610 connected to the oral or nasal cavity of a subject, a second port 620 communicating in this embodiment with atmosphere, first and second fluid paths 630, 640 connectable with the first and second ports 610, 620, and first and second valves 650, 660 operably configured to connect a respective one of the first and second fluid paths 630, 640 with the first and second ports 610, 620. The apparatus further comprises a flow meter 670 for detecting the direction and flow rate through the first port 610. The apparatus still further comprises a gas collection unit 680 located in the second flow path 640 to allow samples to be taken from different phases of the respiratory cycle. In this embodiment the gas collection unit 680 comprises a rotatable body 682 which includes a plurality of collection tubes 684, each forming part of the second flow path 640 on being selectively positioned by rotation of the main body 682.

On-line collection of gases is possible where the subjects are artificially ventilated or by the use of a mask. Sleep apnea and sleep breathing disorders are very common at all ages and the apparatus of the present invention allows sampling of gases in specific phases of exhalation or inhalation. Where sampling is performed through the oropharynx, the concentration of gases sampled through the nasal and oral route can be measured. By virtue of the fact that a sample can be taken during ventilation, spontaneous or artificial, whilst the subject is asleep, anaesthetised or unconscious provides a powerful research tool and can also have clinical applications, for example, in the field of anaesthesia.

Finally, it will be understood that the present invention has been described in its preferred embodiments and can be modified in many different ways without departing from the scope of the invention as defined by the appended claims.

For example, the sampling of collected gases could be made a syringe which is selectively couplable with the collection reservoir. One proposed construction provides a syringe with a valved tip and the collection reservoir with a valved port to which the syringe is connectable. With this construction it is possible for gases first to be collected in the collection reservoir and a sample to be drawn subsequently from the collection reservoir into the syringe and contained therein by closure of the valved tip.

The invention claimed is:

1. An apparatus for collecting airway gases, comprising:
   a mouthpiece through which a user in use exhales to deliver a gas flow therethrough, wherein the mouthpiece is configured to provide a resistance to exhalation which is such as to cause closure of the oropharyngeal velum of the user on exhalation therethrough;
   a first nosepiece which is fluidly connected to the mouthpiece for fitting to one nostril of the user;
   a second nosepiece for fitting to the other nostril of the user;
   a collection device which is fluidly connected to the second nosepiece for collecting airway gases as delivered from the second nosepiece; and
   a scrubber which is fluidly connected to the mouthpiece for removing one or more gases from the gas flow as delivered to the first nosepiece.

2. An apparatus for collecting airway gases, comprising:
   a mouthpiece through which a user in use exhales to deliver a gas flow therethrough, wherein the mouthpiece is configured to provide a resistance to exhalation which is such as to cause closure of the oropharyngeal velum of the user on exhalation therethrough;
   a first nosepiece which is fluidly connected to the mouthpiece for fitting to one nostril of the user;
   a second nosepiece for fitting to the other nostril of the user;
   a collection device which is fluidly connected to the second nosepiece for collecting airway gases as delivered from the second nosepiece; and
   a further collection device which is fluidly connected between the mouthpiece and the first nosepiece for collecting one or more gases from the gas flow as delivered to the first nosepiece, wherein the further collection device comprises a condenser.

3. A method of collecting airway gases, comprising the steps of:
   a user exhaling through a mouthpiece to deliver a gas flow therethrough, wherein the mouthpiece is configured to provide a resistance to exhalation which is such as to cause closure of the oropharyngeal velum of the user on exhalation therethrough;
   fitting a first nosepiece, which is fluidly connected to the mouthpiece, to one nostril of the user;
   fitting a second nosepiece to the other nostril of the user; and
   collecting airway gases as delivered from the second nosepiece in a collection device which is fluidly connected thereto.

4. The method of claim 3, wherein the collection device comprises a collection reservoir.

5. The method of claim 3, wherein the collection device comprises a condenser.

6. The method of claim 3, further comprising the step of:
   removing one or more gases from the gas flow as delivered to the first nosepiece.

7. The method of claim 3, further comprising the step of:
collecting one or more gases from the gas flow as delivered to the first nosepiece in a further collection device which is fluidly connected between the mouthpiece and the first nosepiece.

8. The method of claim 7, wherein the further collection device comprises a collection reservoir.

9. The method of claim 7, wherein the collection device comprises a condenser.

10. The method of claim 3, further comprising the step of: collecting one or more substances from the delivered gas flow in at least one collection element.

11. The method of claim 10, wherein the substance comprises a gas.

12. The method of claim 10, wherein the substance comprises particles.

13. The method of claim 10, wherein the substance comprises micro-organisms or parts thereof.

14. The method of claim 10, wherein any or each collection device includes a collection element.

15. The method of claim 14, wherein the collection element comprises a coating within the respective collection device.

16. The method of claim 14, wherein the collection element is a removable element.

17. The method of claim 16, wherein the collection element is a filter.

18. The method of claim 10, wherein the at least one collection element is a removable element.

19. The method of claim 18, wherein the at least one collection element is disposed downstream of the second nosepiece.

20. The method of claim 18, wherein the at least one collection element is a filter.

21. A method of collecting airway gases, comprising the steps of:
a user exhaling into a mouthpiece, wherein the mouthpiece is configured to provide a resistance to exhalation which is such as to cause closure of the oropharyngeal velum of the user on exhalation thereinto;
fitting a nosepiece to one nostril of a nasal airway of the user;
providing a gas flow through the nasal airway of the user from the other nostril to the one nostril of the user while the oropharyngeal velum of the user is closed; and
collecting airway gases as delivered from the nosepiece in a collection device which is fluidly connected thereto.

22. The method of claim 21, wherein the collection device comprises a collection reservoir.

23. The method of claim 21, wherein the collection device comprises a condenser.

24. The method of claim 21, further comprising the step of:
collecting one or more gases from the exhaled gas flow as delivered to the mouthpiece in a further collection device which is fluidly connected thereto.

25. The method of claim 24, wherein the further collection device comprises a collection reservoir.

26. The method of claim 24, wherein the further collection device comprises a condenser.

27. The method of claim 21, further comprising the step of:
collecting one or more substances from the gas flow in at least one collection element which is disposed downstream of the nosepiece.

28. The method of claim 27, wherein the substance comprises a gas.

29. The method of claim 27, wherein the substance comprises particles.

30. The method of claim 27, wherein the substance comprises micro-organisms or parts thereof.

31. The method of claim 27, wherein any or each collection device includes a collection element.

32. The method of claim 31, wherein the collection element comprises a coating within the collection device.

33. The method of claim 31, wherein the collection element is a removable element.

34. The method of claim 33, wherein the collection element is a filter.

35. The method of claim 27, wherein the at least one collection element is a removable element.

36. The method of claim 35, wherein the at least one collection element is a filter.

* * * * *

UNITED STATES PATENT AND TRADEMARK OFFICE
CERTIFICATE OF CORRECTION

| | |
|---|---|
| PATENT NO. | : 7,377,901 B2 |
| APPLICATION NO. | : 10/312242 |
| DATED | : May 27, 2008 |
| INVENTOR(S) | : Djupesland et al. |

Page 1 of 1

It is certified that error appears in the above-identified patent and that said Letters Patent is hereby corrected as shown below:

On the Title Page Item (56), under References Cited, please add the following text:

FOREIGN PATENT DOCUMENTS
95/31721    11/1995    WIPO    G01N/33/497
99/57560    11/1999    WIPO    G01N/33/497

Signed and Sealed this

Seventeenth Day of February, 2009

JOHN DOLL
*Acting Director of the United States Patent and Trademark Office*